Jan. 21, 1936. E. E. STATTER Re. 19,829

SANITARY NAPKIN BELT

Original Filed March 9, 1929

Inventor

Estella Statter

By Lynn H. Latta Attorney

Reissued Jan. 21, 1936 Re. 19,829

UNITED STATES PATENT OFFICE 19,829

SANITARY NAPKIN BELT

Estella E. Statter, Sioux City, Iowa, assignor to Humphrey Statter Jr., Sioux City, Iowa Original No. 1,782,152, dated November 18, 1930, Serial No. 345,680, March 9, 1929. Application for reissue November 18, 1932, Serial No. 643,256

5 Claims. (Cl. 128—291)

My invention relates to sanitary napkins and has for its object to provide a buckle of novel, durable, and inexpensive construction for use in connection with a sanitary napkin belt.

Another object of my invention is to provide such a buckle which cannot cause injury to the body of the wearer.

A further object is to provide a buckle construction which is particularly adapted to secure the cheese cloth envelope of the napkin in such a way as to positively prevent slipping of the napkin relative to the buckle.

Another object is to provide such a buckle to or from which the napkin may be attached or detached with a minimum of difficulty.

With these and other objects in mind, my invention consists in the construction, arrangement, and combination of the various parts of my device, whereby the objects contemplated are attained, as hereinafter more fully set forth, pointed out in my claims, and illustrated in the accompanying drawing, in which:

Figure 1:
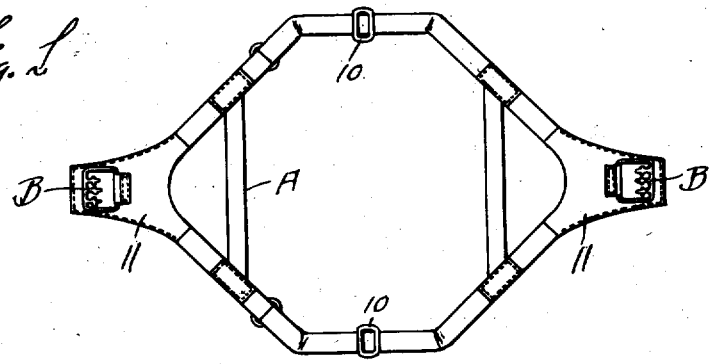
Fig. 1 is a view of a belt embodying by invention.

I have used the reference character A to indicate generally the belt, which is adapted to encircle the body of a wearer and which is provided with appropriate clasps 10 for adjusting the length of the band.

The supporter embodies a pair of diametrically opposed pads or supports 11, which form part of the buckle assembly, serving principally to support the buckle members B. The latter are secured hingedly to the support as by means of the hinge sleeves 12.

Each buckle includes a closed loop comprising an upper portion 14, attached to the support 11, side arms 13 depending therefrom, and a lower or cross member 15 connecting said arms 13. Prongs 16 are formed integrally with the lower member 15 and extend into the space with the loop, substantially parallel with each other and with the side arms 13. The end of the napkin 17, which is of cheese cloth, in the ordinary commercial article, is passed through the loop from rear to front, and upon being pulled downwardly, will pass over the prongs 16, the latter piercing the loose mesh of the cheese cloth. It may be noted that in order to facilitate passing the end of the napkin through the loop, the latter may be lifted to a horizontal position with one finger of one hand while the support is pressed against the body of the wearer by the remaining fingers of the same hand to hold the buckle steady, and the other hand may be used to pass the end of the napkin upwardly through the loop.

The prongs are provided with laterally projecting lugs 18, which are adapted to pass entirely through the cheese cloth of the napkin and to hold the napkin against movement toward the ends of the prongs.

The pull of the body portion of the napkin and the opposing pull of the belt supplement the retaining function of the lugs in holding the napkin against release from the prongs.

Figure 2:
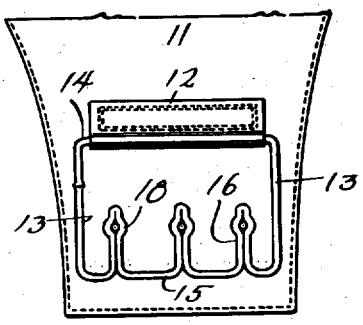
Fig. 2 is an enlarged view of the buckle.
Figure 3:
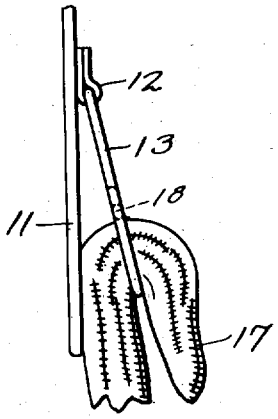
Fig. 3 is a side elevation of the buckle.

It will be understood that it is possible for the buckle to come into contact with the body of the wearer during physical exertion especially, and one of the basic objects of my invention has been to make a buckle construction which will not injure the body of the wearer. This result is achieved primarily by constructing the prongs 16 integrally with the loop of the buckle, and lying within the loop, in the plane thereof, whereby the loop constitutes a guard for the prongs. I find that the prongs may be rounded off slightly as shown in Fig. 2, and the lugs 18 may also be rounded off, without interfering with the penetrating ability of the prongs, or the retaining ability of the lugs.

This is due to the fact that the material of the napkin is flexible enough to close around the shanks of the prongs after the lugs 18 have passed through the material. As has been noted before, the retaining action of the lugs is supplementary to the pull of the body of the napkin.

The buckle may be formed of sheet metal, or other sheet material, stamped and finished to remove its jagged edges.

An additional protective measure may be employed, consisting in coating the side arms 13 and lower member 15 of the buckle with rubber.

By forming the lugs at a distance from the rounded tip, the mesh of the cheese cloth is first spread by the tip, and then by the lug.

I claim as my invention:

1. In a sanitary napkin belt, in combination with a pad, a hinge sleeve secured thereto and positioned horizontally when the belt is being worn, and a buckle comprising a closed loop having spaced portions one of which is received in the hinge sleeve, prongs formed integrally with the other portion and extending into the space within the loop, substantially in the plane of the loop, each of said prongs having a rounded tip and a laterally projecting lug spaced from said tip.

2. In a sanitary napkin belt, in combination with a pad, a hinge sleeve secured thereto and positioned substantially horizontally when the belt is being worn, and a buckle comprising a closed loop having spaced portions, one of which is received in the hinge sleeve, prongs formed integrally with the other portion and extending into the space within the loop, substantially in the plane of the loop, each of said prongs having a rounded tip.

3. In a sanitary napkin belt, the combination with a support depending from the belt when the latter is being worn, of a buckle comprising a loop having an upper portion hinged to the support, integrally formed side arms depending from said upper portion, and an integral lower portion connecting said side arms; and a prong formed integrally with said lower portion and extending upwardly into the space within the loop, in the plane of the loop, whereby the loop acts as a guard for said prong to prevent contact thereof with the skin of a wearer, said prong being of greater length than its width at its base, whereby it may pass entirely through the end of a sanitary napkin.

4. In a sanitary napkin belt, in combination with a support, depending from the belt when the latter is being worn, a buckle comprising a closed loop having an upper horizontal portion hinged to the support, the remainder of the buckle depending therebelow, integrally formed side arms depending from said upper portion, an integral lower portion connecting said side arms, and prongs formed integrally with the lower portion and extending upwardly into the space within the loop in the plane of the loop, said prongs being formed near their upper ends with opposed laterally projecting lugs spaced from the tips of the prongs, said lugs being rounded but forming well defined shoulders between their lower edges and the adjacent side edges of the prongs.

5. In a sanitary napkin belt including a support which depends when the belt is being worn, a buckle comprising a closed loop having an upper portion hinged to the support, integrally formed side arms depending from said upper portion, an integral lower portion connecting said side arms, and a prong formed integrally with said lower portion and projecting upwardly into the space within the loop in the plane of the loop, said prong being formed near its upper end with opposed lugs projecting laterally in the plane of the loop and spaced from the tip of the prong, said prong being of greater length than its width at its base, whereby it may pass entirely through the end of a sanitary napkin.

ESTELLA E. STATTER.